United States Patent [19]

Dern

[11] Patent Number: 5,671,648
[45] Date of Patent: Sep. 30, 1997

[54] ROTARY MICROTOME WITH HORIZONTAL SWEEP

[76] Inventor: Klaus Dern, 4645 Dunwoody Dr., Dunwoody, Ga. 30350

[21] Appl. No.: 586,181

[22] Filed: Jan. 16, 1996

[51] Int. Cl.[6] .............................. G01N 1/06; B26D 7/06
[52] U.S. Cl. .................. 83/411.1; 83/411.3; 83/414; 83/733; 83/915.5
[58] Field of Search ............................. 83/267, 411.1, 83/411.2, 411.3, 411.4, 411.5, 411.6, 410.8, 410.9, 733, 915.5, 414

[56] References Cited

U.S. PATENT DOCUMENTS

| | | | |
|---|---|---|---|
| 1,797,694 | 3/1931 | Ott | 83/915.5 X |
| 2,482,853 | 9/1949 | Ladd | 83/915.5 X |
| 2,642,774 | 6/1953 | Picard et al. | 83/915.5 X |
| 2,746,264 | 5/1956 | Keyes | 83/915.5 X |
| 2,753,761 | 7/1956 | Hillier | 83/915.5 X |
| 2,795,998 | 6/1957 | Gorham et al. | 83/411.3 |
| 2,797,616 | 7/1957 | Gettner et al. | 83/915.5 X |
| 2,843,014 | 7/1958 | Sitte | 83/915.5 X |
| 2,875,669 | 3/1959 | Sjostrand et al. | 83/915.5 X |
| 3,091,144 | 5/1963 | Villalobos | 83/915.5 X |
| 3,191,477 | 6/1965 | Danon | 83/915.5 X |
| 3,902,390 | 9/1975 | Darbo | 83/915.5 X |

FOREIGN PATENT DOCUMENTS

| | | | |
|---|---|---|---|
| 182540 | 7/1955 | Austria | 83/915.5 |
| 187706 | 11/1956 | Austria | 83/915.5 |
| 654123 | 6/1951 | United Kingdom | 83/915.5 |

*Primary Examiner*—Rinaldi I. Rada
*Assistant Examiner*—Clark F. Dexter
*Attorney, Agent, or Firm*—Harry I. Leon; Vivian L. Steadman

[57] ABSTRACT

A microtome having a rotatable platform and a fixedly mounted cutting blade which is disposed perpendicularly to the axis of a shaft about which the platform rotates. With each rotation, it carries the specimen holder beneath the blade. The height of the cutting edge of the blade relative to a specimen mounted atop the holder determines the thickness of any section cut therefrom. After each cut, the holder can be automatically raised in height by a predetermined increment to allow another section of the same thickness to be cut. Mechanisms are also provided which eliminate play in both the radial and axial directions between a cylindrical housing supporting the platform and the shaft, so that the microtome can be used to make extremely precise cuts of specimens. Not only can it precisely cut specimens in sizes accommodated by either the rotary or base-sledge microtomes of the prior art but also the microtome according to the present invention can precisely cut specimens which are too large for either of these earlier machines. Moreover, with it, an operator can load a specimen while keeping his hands at a considerable distance from and out of line with the cutting blade, substantially reducing the risk of his exposure to deadly diseases as a result of a blade-related injury.

5 Claims, 6 Drawing Sheets

ROTARY MICROTOME WITH HORIZONTAL SWEEP

BACKGROUND OF THE INVENTION

Microtomes are precision-mechanical devices for cutting samples into sections for microscopic examination. In the prior art, microtomes can be grouped into two basic categories: rotary and base-sledge. The former have an up and down cutting stroke and the latter a back and forth horizontal cutting stroke. The maximum size of a specimen that can be sectioned in these devices is limited in part by the fact that the travel of the blade during a cutting stroke is approximately 200 mm in the base-sledge microtomes and only 50 mm in the rotary microtomes. Further, many of these earlier microtomes utilize a blade which, after cutting a specimen, does not clear it but rather picks up and compresses it during the return stroke.

Rotary microtomes in which the specimen holder or, alternatively, the blade is retracted from the plane of the cutting stroke so that the blade will not contact the specimen on the return stroke are also known. Examples of such microtomes can be found in U.S. Pat. No. 4,967,629, which was issued to Behme on Nov. 6, 1990, and in U.S. Pat. No. 4,505,175, which was issued to Reichel on Mar. 19, 1985.

Earlier, in U.S. Pat. No. 3,902,390, issued on Sep. 2, 1975, Darbo disclosed a rotary microtome which lacks means for retracting the blade and relies instead on a generally horizontal cutting motion. Of lightweight construction intended for field use, this microtome utilizes a blade holder which is rotated about a metering post and carries the cutting edge of the blade around and over the specimen in a plane normal to the axis of the metering post. The height of the cutting edge relative to the specimen is set by manually adjusting the metering post. Unfortunately, the limited accuracy of Darbo's microtome severely restricts its use, making it unsuitable for cutting extremely thin sections.

On the other hand, those microtomes known in the prior art to be capable of cutting these extremely thin sections are perilous to load. Upon mounting the sample holder in these microtomes, a medical worker must bring his hand within about 1 inch of—dangerously close to—the blade. In such a situation, extreme caution is required; otherwise, the operator may cut himself and risk contracting AIDS or the like.

SUMMARY OF THE INVENTION

The primary object of the present invention is to provide a machine for cutting extremely thin sections as is currently needed in routine medical laboratory and biological research work as well as in materials science and microscopic materials testing.

A further object of this invention is to provide, in a single machine, the capabilities of both the rotary and base-sledge microtomes of the prior art and to provide a microtome which can cut, with extreme precision, both standard specimens and specimens that are too large for microtomes of the prior art.

A still further object of this invention is to provide such a microtome in which the blade is never in contact with the specimen except to cut it and, moreover, neither the specimen holder nor the blade needs to be retracted from the specimen after it has cut it.

A still further object of this invention is to provide a microtome that can be used safely because not only does the knife edge of its cutting blade face away from the operator as he is loading a specimen but also the sample holder in the microtome is located at a considerable distance from the blade.

A still further object of this invention is to provide a microtome in which the sample can be frozen easily since it is held horizontally.

A still further object of this invention is to offer a long-lived, maintenance-free machine which is equipped with extremely rigid blade and specimen holders capable, at the same time, of extremely accurate thin section cutting.

The rotary microtome of the present invention comprises a blade holder, a platform generally in the form of a cylindrical disk on the top of which is mounted a specimen holder, means including a base and a stationary vertical shaft rigidly attached thereto for rotatably receiving the platform, and means including a blade holder support mounted on the vertical shaft and a base-mounted post for suppporting both ends of the blade holder. The base-mounted post is disposed outside of the path traversed by the platform as it rotates about the vertical shaft. Having the blade holder thus supported adds greatly to its rigidity and consequently to the accuracy with which the blade can cut.

Extending downwardly from the platform is a hollow cylindrical housing which preferably is formed as an integral unit therewith. A close slip fit between the housing and the vertical shaft is achieved with the use of a first heavy duty but lightly loaded, high precision roller bearing disposed therebetween. In the preferred embodiment, the bearing is press-fitted into the cylindrical housing proximate with the lower end thereof.

Means for reducing the amount of play in either a radial or axial direction between the housing and the vertical shaft is also provided. The play reducing means includes the vertical shaft having a short tapered section with an upwardly inclined wall disposed at an angle of about 45 degrees to the vertical. In the preferred embodiment, the lower edge of the inner race for the first roller bearing pushes downwardly against the inclined wall. In the process, the inner race of this first roller bearing most likely skews slightly, causing a realignment in the positions of its rollers; in any event, play in the radial direction between the housing and shaft is virtually eliminated.

The play reducing means further includes a retainer washer rigidly attached to the blade holder support, the retainer washer having a short tapered section with a downwardly inclined wall disposed at an angle of about 45 degrees to the vertical. Preferably, a second heavy duty but lightly loaded, high precision roller bearing is also disposed between the shaft and housing, press-fitted thereinto proximate with the downwardly inclined wall of the retainer washer. Located upwardly of the upper end of the vertical shaft, this downwardly inclined wall pushes against the upper edge of the inner race for the second roller bearing press-fitted into the cylindrical housing, most likely causing the inner race of the latter bearing to skew slightly and simultaneously to realign its rollers, so that this realignment in combination with that of the rollers in the first roller bearing eliminates any play in the radial direction between the housing and shaft.

Means for reducing the axial motion of the platform includes a thrust shim plate juxtaposed between the upper end of the vertical shaft and the retainer washer. Slidably received by the retainer washer and threadedly engaged by the upper end of the shaft, a retainer screw is employed to hold the blade holder support, retainer washer and shaft in assembled relation. Moreover, the retainer screw comprises means for pressing the inner race of the first roller bearing against the tapered section of the shaft and the inner race of the second bearing against the tapered portion of the retainer washer contiguous thereto. That is, upon tightening the retainer screw, not only is the end of the shaft brought into contact with the thrust shim plate but also the inclined walls of the shaft and retainer washer are pressed into the inner race of each roller bearing contiguous therewith.

The preferred thickness for this thrust shim plate is determined through trial and error. Experience has shown that with a bronze thrust shim plate of the proper thickness, play between the housing and shaft in both the radial and axial directions can be eliminated upon tightening the retainer screw with only a small amount of pressure applied to the thrust shim plate.

The microtome according to the present invention further comprises drive means for rotating the platform on which the specimen holder is mounted, so that the specimen can be moved along a horizontal sweep into the cutting blade. In the preferred embodiment, even with nearly zero tolerance between each roller bearing and the vertical shaft, the platform still offers little resistance to being turned. The drive means comprises a drive belt, a first belt sprocket which engages the belt and is fixedly attached to the cylindrical housing, a weighted and balanced handwheel rotatable about a horizontal axle supported by bearings mounted in a side frame of the base, and a pair of mating bevel gears. One of these bevel gears is attached to the end of the horizontal axle distal from the handwheel; the other bevel gear is mounted on a first vertical axle supported by a first bearing block secured to the base. Also mounted on the first vertical axle is a second belt sprocket which, in the assembled microtome, is engaged by the same drive belt as is the first belt sprocket. The weighted and balanced handwheel gives the platform an easy steady turning motion, thereby minimizing the effects of cutting on the specimen as it is being moved, supported by the specimen holder, into the cutting blade.

Means for adjusting tension on the drive belt comprises a third belt sprocket on one end of a second vertical axle aligned in parallel with the first vertical axle. The second vertical axle engages a second bearing block mounted on a structure having elongated holes for receiving bolts threadedly engageable with the base. With the use of these elongated holes, the position of the third belt sprocket can be moved, allowing the tension on the drive belt to be adjusted.

For applications involving the preparation of a large number of sections from a single specimen, the drive means also includes a motor drive. In an alternative embodiment, the motor drive is positioned so as to take the place of the second vertical axle. However, for most applications, the manually driven handwheel is adequate.

In the microtome according to the present invention, the blade holder is elongated having one end thereof mounted on a post secured to the base and the other end thereof supported by the vertical shaft, with the holder spanning the radius of the platform and the cutting blade having a similar span. The blade is held perpendicularly to the path traversed by the specimen holder so that it moves beneath the blade holder each time the platform is turned through 360 degrees.

The blade holder includes means for adjusting the angle at which the blade is inclined with respect to the horizontal plane. Moreover, the angle of contact between the blade itself and the specimen can be adjusted, so that materials of widely differing hardness can be accommodated in the microtome according to the present invention. Further, the latter machine allows especially large specimens can be sectioned. With the platform measuring, by way of example, about 10.75 inches (27 cm) in diameter, specimens as large as 4 inches (10 cm) in length can be cut.

In the present invention, means for raising the specimen holder in a series of predetermined incremental amounts is also provided. After the specimen has been passed through the blade, the raising means elevates the specimen holder by a distance corresponding to the thickness of the next specimen to be cut. Mounted on a hollow column supported by a fine thread screw, the specimen holder is moved upwardly as the screw is turned in the forward direction raising the column. Means for turning the fine thread screw to raise or lower the specimen holder includes a stepper motor supported by a suitable gear train, a motor driver for delivering power to the motor, and a controller for taking commands from the operator of the microtome. Mounted on the underside of the platform, the stepper motor with its gear train gets power from and is controlled by a plurality of slip rings. The slip rings are fastened to the cylindrical housing.

In the preferred embodiment, each revolution of the fine thread screw raises the specimen holder 1 mm and the stepper motor is programmed for 1000 steps per revolution, thus providing an incremental change of 1 micron in the height of the specimen holder per step.

Preferably, a user friendly control panel is also furnished to allow the operator to set the height of each cut easily. With this panel, the operator can set the desired thickness of an individual sample section and have the stepper motor automatically raise the specimen holder by this distance. Moreover, in the preferred embodiment, once a section has been cut, the specimen must travel approximately 90 degrees before the stepper motor can again be turned on and move the specimen holder upwardly by the desired increment of height, automatically raising the specimen holder to accommodate the next cut.

In preparation for using the microtome according to the present invention, a specimen embedded in paraffin or plastic is mounted in the specimen holder. As the specimen is being mounted in the holder, the platform is rotated so that it rotated away from the blade by approximately 180 degrees. In the preferred embodiment, the platform is sufficiently large that the operator's hand need not be any closer to the blade than about 12 cm, virtually eliminating the chance for injury. Once the specimen is loaded into the holder, trimming controls are preferably used to raise it quickly to trim the specimen. Then the operator simply sets a scale on the controller and gets a digital readout of the selected cutting thickness which in the preferred embodiment can range from between 0.5 micron and 100 microns.

DETAILED DESCRIPTION OF THE PREFERRED EMBODIMENT

Figure 6:
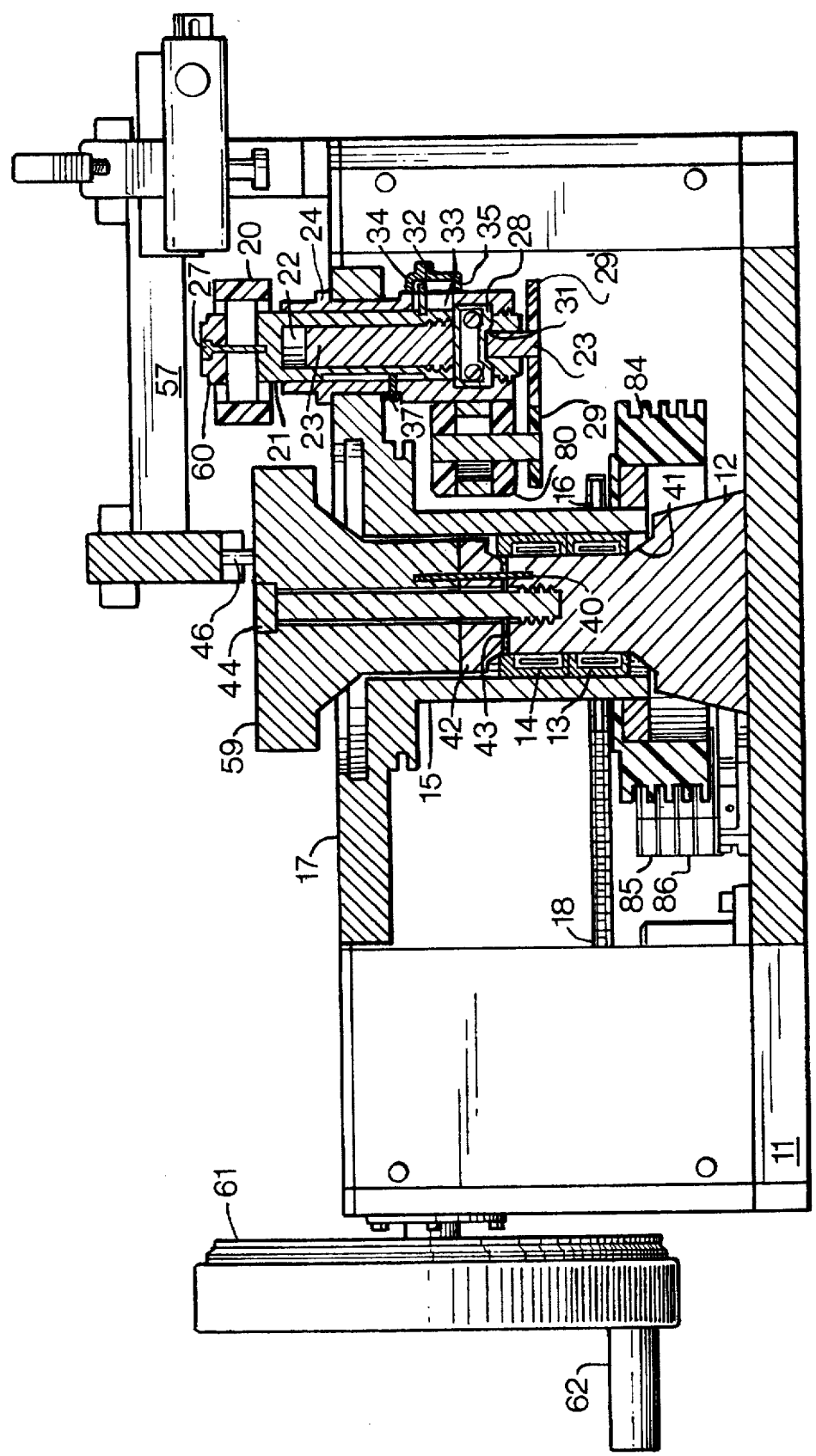
FIG. 6 is a cross section taken on line 6—6 of FIG. 5.

In the drawings, a rotary microtome in accordance with the present invention is referred to generally by the numeral 10. As best shown in FIG. 6, the microtome 10 comprises a base 11 which supports a vertical, non-rotating shaft 12, a retainer washer 42, and a blade holder support 59. Rotatable about the shaft 12 is a hollow cylindrical housing 15 into which are press-fitted two heavy duty precision bearings 13, 14, preferably roller bearings. Mounted on the outside surface of the housing 15 is a belt sprocket 16 and on the top of the housing, a platform 17. The platform 17 and the housing 15 are fixedly attached to each other and turn as a unit when a drive belt 18 engages the sprocket 16. The retainer washer 42, which is connected to the shaft 12 by a screw 44 threadedly engaged therewith is employed to hold the housing 15 and shaft in assembled relation. A first location pin 40, slideably received by the shaft 12, the retainer washer 42, and the blade holder support 59, prevents the latter from turning relative to the shaft.

Secured to a non-rotatable hollow column 21 with a screw 27, a specimen holder 20 is mounted on the platform 17 proximate with the outer edge thereof (FIG. 6). Slideably received by a hollow support 24, the column 21 itself defines a hole 22 having threads formed therein for receiving the upper end of a threaded shaft 23. The lower end of the shaft 23, which is received by a bearing 28 mounted within the hollow support 24, is free to rotate. When the shaft 23 is turned, the column 21 is moved up (or down) within the hollow support 24. A second location pin 37, which is restrained to move along a vertical groove formed in the outer wall of the column 21, prevents it from rotating with the shaft 23.

A stepper motor 80 mounted externally of the hollow support 24 is mechanically connected to the shaft 23 by a mating pair of gears 29, 29' (FIG. 6). A suitable stepper motor is the Oriental Motor model UFK544AA, available commercially from Oriental Motor U.S.A. Corp. in Torrance, Calif. When the stepper motor 80 is activated, the shaft 23 also turns, raising (or lowering) the column 21 and with it the specimen holder 20.

In the preferred embodiment, each revolution of the shaft 23 raises the specimen holder 1 mm and the stepper motor 80 is programmed for 1000 steps per revolution, thus providing an incremental change of 1 micron in the height of the specimen holder 20 per step.

Figure 3:
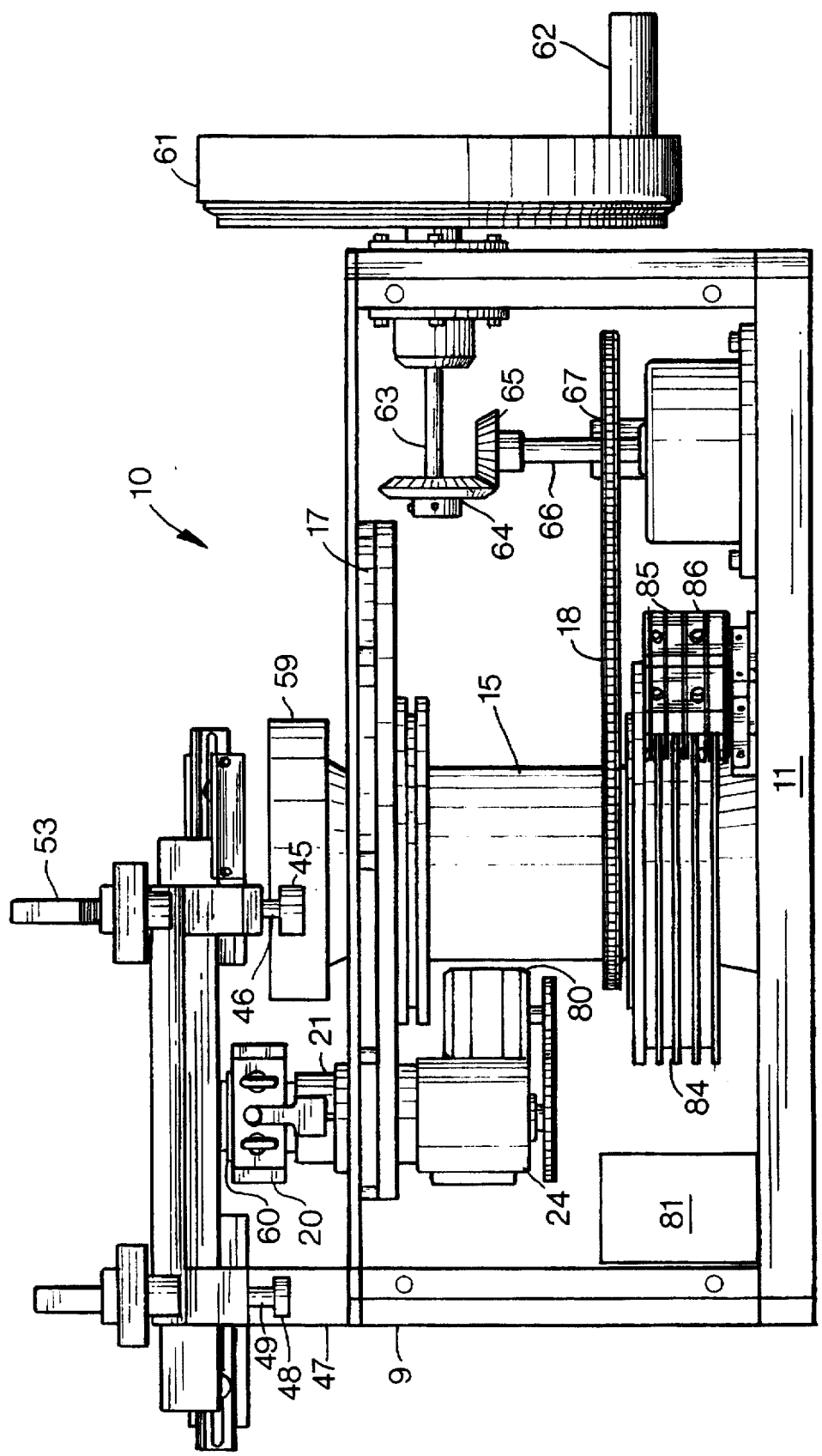
FIG. 3 is a front elevation view of the microtome according to FIG. 1 with the front cover removed.
Figure 4:
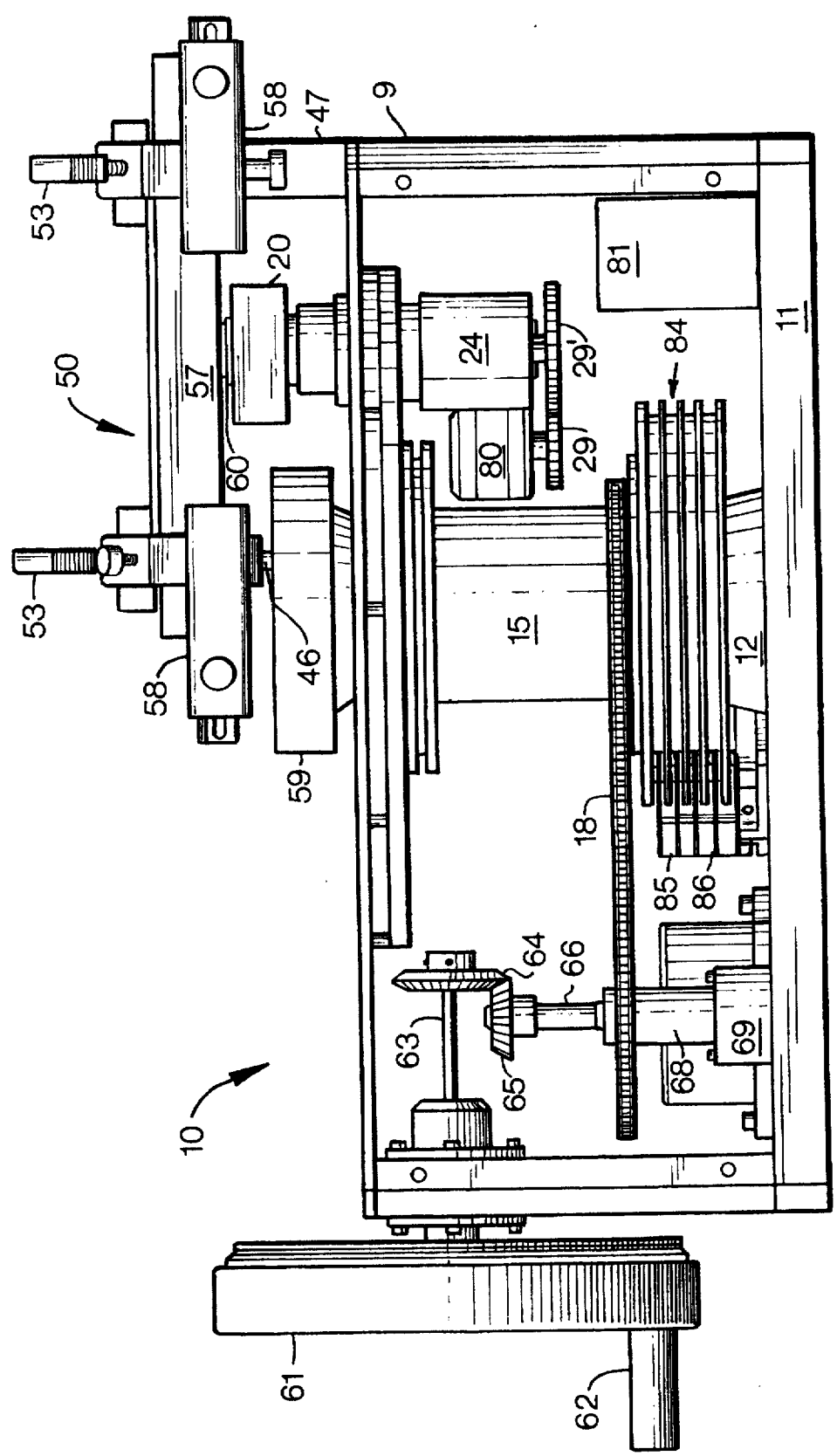
FIG. 4 is a back elevation view of the microtome according to FIG. 1 with the back panel removed.

The stepper motor 80, which moves with the platform 17, receives power from a motor driver 81 (FIGS. 3 and 4). Electrical connections between the motor 80 and the motor driver 81 are made by a pair of multi-contacts 85, 86 and slip rings 84 mounted on the cylindrical housing 15. In the preferred embodiment, the stepper motor uses five wires for control and two wires for a pair of limiting switches 34, 35. A suitable slip ring and brush assembly is the seven ring model No. CAY-94 available commercially from Airflyte Electronics Co.

Means for limiting the travel of the specimen holder 20 in a vertical direction includes upper and lower limit switches 34, 35. Activated upon contact with a guide pin 32, each of the limit switches 34, 35, similarly to the motor 80, is connected to the motor driver 81 through the slip rings 84 and contacts 85, 86.

The microtome 10 further comprises an elongated blade holder 50, a cutting blade 57, and means for adjusting the angle at which the blade is inclined with respect to the horizontal plane. Spanning most of the platform 17 outwardly from its rotational center, the blade holder 50 is mounted with its opposing ends secured to the blade holder support 59 and a block 47 affixed to post 9 (FIGS. 3 and 4). The cutting blade 57 has a similar span and is held perpendicularly to and slightly above the path traversed by the specimen holder 20 so that it moves beneath the blade holder 50 each time the platform 17 is turned through a rotation of 360 degrees.

Moreover, the microtome 10 includes means for adjusting the angle of contact between the blade 57 and a specimen 60, so that materials of widely differing hardness can be sectioned. To allow for this adjustment, the heads of downwardly extending bolts 46 and 49 affixed to opposing ends of the blade holder 50 are simultaneously retained in and movable, with sufficient effort, along open-ended, elongated channels 45 and 48, respectively, formed in the support 59 and the block 47, respectively. The channels 45, 48 themselves are aligned generally parallel to the path traversed by the specimen holder 20 as it moves beneath the blade holder 50.

Figure 5:
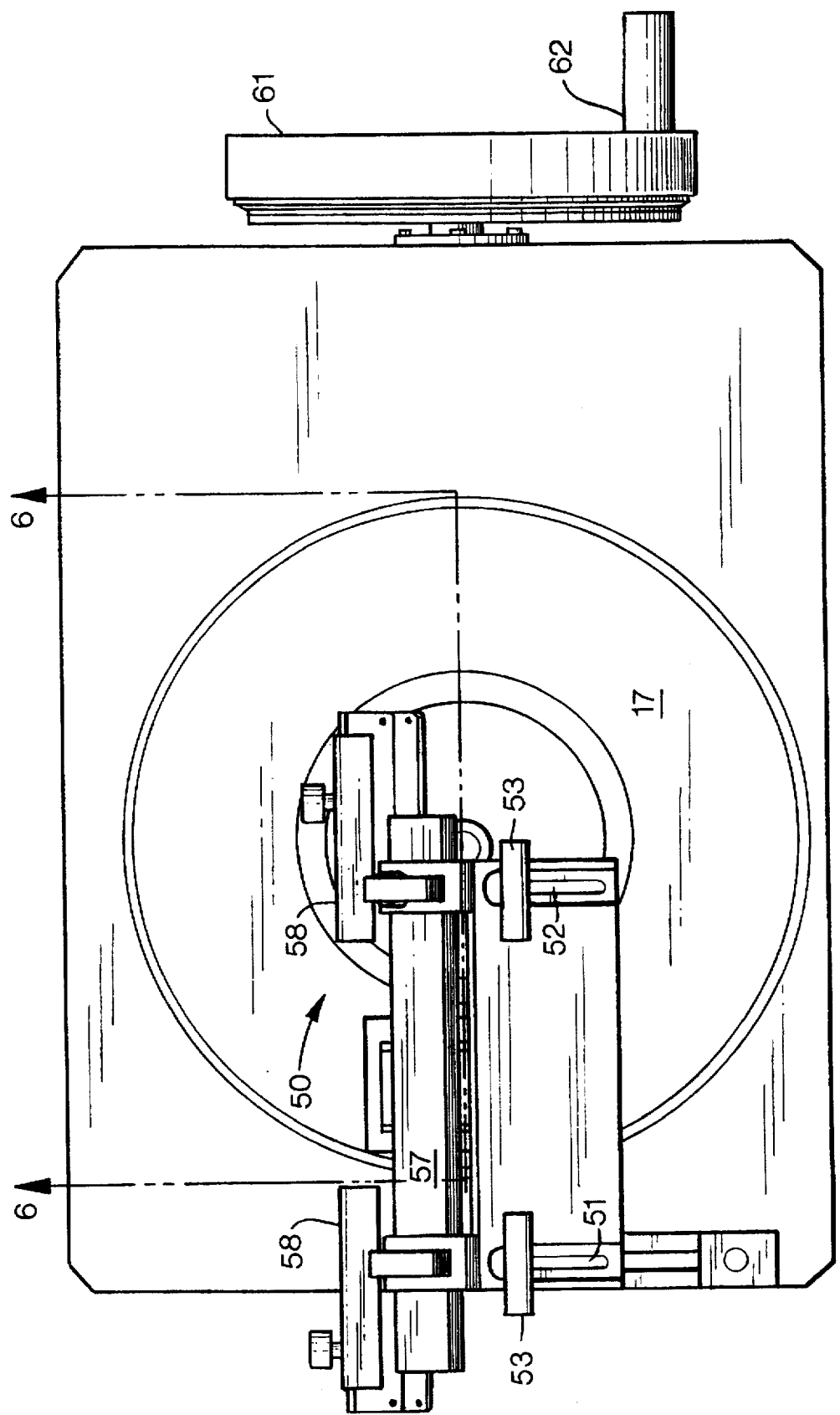
FIG. 5 is a top plan view of the microtome according to FIG. 1.

In addition, the blade holder 50, as is standard in microtomes of the prior art, defines two elongated mounting slots 51, 52(FIG. 5). In the microtome 10, the mounting slots 51, 52 receive the shanks of the bolts 49, 46, respectively. Together the bolts 49, 46 and wing nuts 53, which are threadedly engageable therewith and can be tightened without the use of tools, maintain the holder 50, block 47 and support 59 in assembled relation. Thus the slots 51, 52, in combination with the channels 48, 46 allow the angle of contact between the cutting blade 59 and the specimen 60 to be adjusted over a wide range.

The blade holder 50 also includes means, commonly employed in microtomes of the prior art, for setting the blade 57 at differing angles with respect to the horizontal plane, thus giving the microtome 10 flexibility in cutting a wide variety of specimens.

In the preferred embodiment, the blade holder 50 is also provided with a pair of safety shields 58 for protecting persons from injury by contact with the blade 57, especially the operator when he is loading and unloading a specimen 60 from the holder 20.

In order to hold a high degree of accuracy during sectioning, the microtome 10 comprises means, including short tapered sections formed on the vertical shaft 12 and on the retainer washer, for reducing the amount of play in a radial direction between the cylindrical housing 15 and the vertical shaft 12. To reduce play in such a direction, adjustments are made in the positions of the rollers within the bearings 13, 14, heavy duty but lightly loaded bearings juxtaposed between the cylindrical housing 15 and the shaft 12.

In particular, in the assembled microtome 10, the lower edge of the inner race of the bearing 13 presses against the tapered section 41 which, in longitudinal cross-section, inclines outwardly and downwardly at an angle of about 45 degrees to the vertical (FIG. 6). Similarly, the retainer washer 42 has an inclined wall which presses downwardly against the upper edge of the inner race of the bearing 14. This inclined wall, in longitudinal cross-section, also slopes outwardly but upwardly at an angle of about 45 degrees to the vertical (FIG. 6). By trial and error, one can utilize the screw 44 to adjust the force with which the bearing 13 presses against the tapered section 41 and with which the retainer washer 42 presses against the bearing 14 in such a way that any play in the radial direction between the housing 15 and shaft 12 is eliminated.

Means for eliminating the axial motion of the platform 17 includes an annular thrust shim plate 43. The thrust shim plate 43, which is preferably fabricated of bronze, measures, by way of example, about 1 to 2 mm in thickness. Placed between the upper end of the vertical shaft 12 and the bottom surface of the retainer washer 42, the thrust shim plate 43 is slideably received by the screw 44 as well as by the first location pin 40. As the screw 44 is tightened, the tapered section 41 of the shaft 12 and the inclined wall of the retainer washer 42 are pressed into the inner races of bearings 13, 14 respectively; and the upper end of the shaft 12 comes into contact with the thrust shim plate 43. With a shim plate 43 of suitable thickness and composition, all play in the axial direction between the cylindrical housing 15 and the shaft 12 can be eliminated by properly tightening the screw 44.

Similarly, play between the shaft 23 and the column support 24 can be reduced with the use of a tapered section 31 threadedly engaged with the lower end of the column support. In longitudinal cross-section, the tapered section 31 inclines outwardly and downwardly at an angle of about 45 degrees to the vertical (FIG. 6). In the assembled microtome 10, the lower edge of the inner race of a bearing 28, juxtaposed between the column support 24 and the shaft 23, presses against the tapered section 31 in such a way that play in the radial direction between the shaft and column support is virtually eliminated.

In use, the microtome 10 can be manually operated by turning a handwheel 61 mechanically linked to the platform 17 (FIGS. 3,4). Equipped with a handle 62 attached proximate with its outer periphery, the handwheel 61 is weighted and balanced so as to minimize the effects of cutting on the specimen 60 as it is being advanced into the cutting blade 57, giving the microtome an easy steady motion as the platform is being turned.

As is best illustrated in FIG. 4, the handwheel 61 and the platform 17 are mechanically linked by a pair of mating bevel gears 64, 65, one of which, like the handwheel, is attached to a horizontal axle 63 supported by bearings in the side frame of the microtome (FIG. 4). The other bevel gear is affixed to a first vertical axle 66 rotatably supported by a bearing block secured to the base 11. As the handwheel 61 is turned, gears 64 and 65 engage, causing a belt sprocket 67 mounted on the axle 66 to turn as well as the drive belt 18.

Not only is the drive belt 18 placed on belt sprockets 16 and 67 attached to the housing 15 and axle 66, respectively, but also on a belt sprocket (not shown) mounted on the upper end of a second vertical axle 68. The axle 68 itself is rotatably supported by a bearing block 69 which defines a plurality of elongated mounting holes (not shown). Bolts which are received by the elongated mounting holes fasten the block 69 to the base 11. With the use of the elongated mounting holes, the block 69 can be repositioned relative to the base 11 so as to adjust the tension on the drive belt 18.

In use, the platform 17 can be turned enough times, by manually turning the handwheel 61 with the handle 62, to carry out most sectioning operations. For very large serial operations, on the other hand, the handwheel 61 can be easily supplemented by the use of a motor (not shown) positioned so as to take the place of the second vertical axle 68.

Figure 1:
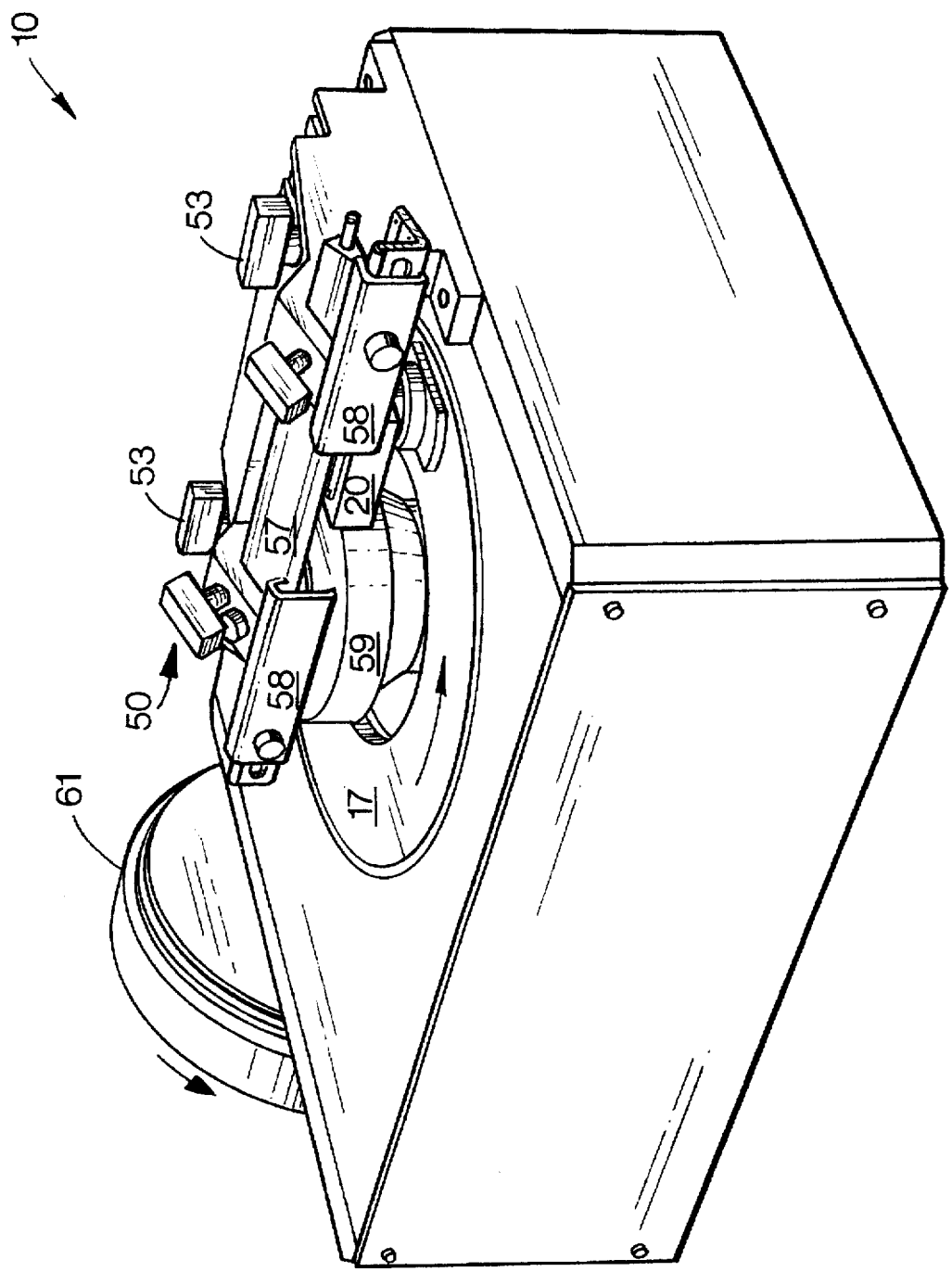
FIG. 1 is a top right side perspective view of the microtome according to the present invention.
Figure 2:
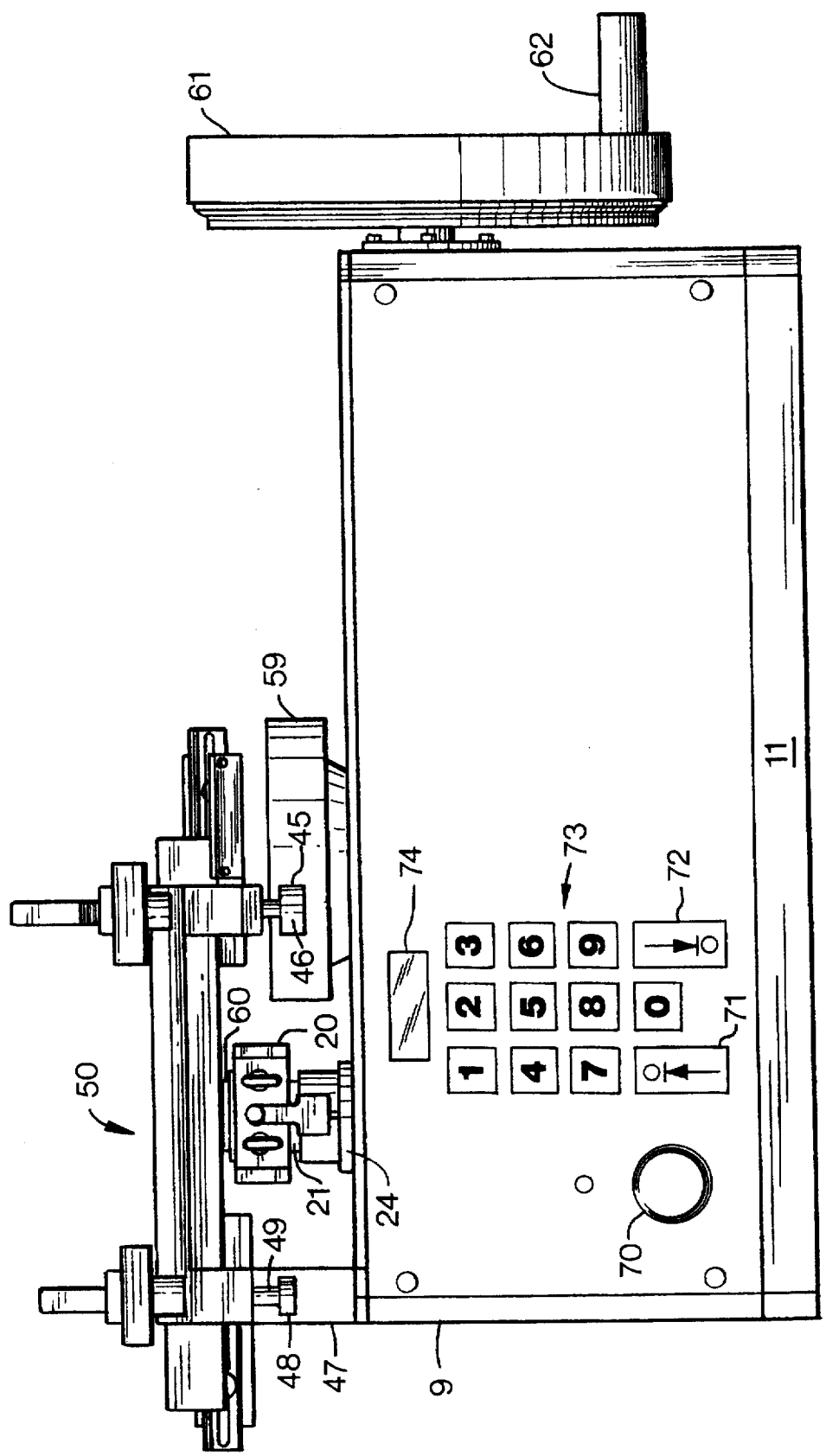
FIG. 2 is a front elevation view of the microtome according to FIG. 1.

In the preferred embodiment, the microtome also includes a control panel with a trimming switch 70, an "up" direction switch 71, a "down" direction switch 72, and a keyboard 73 which is calibrated in microns (FIG. 2). The control panel take commands from whomever is operating the microtome 10 and translates them into electronic signals which are then fed into a controller (not shown) for the motor driver 81. A suitable controller for use with the driver 81 is model No. SI-1 available commercially from Applied Motor Products.

To section a specimen 60, the operator first places it in the specimen holder 20. Utilizing the trimming switch 70, together with the direction switches 71, 72, he then roughly adjusts the height of the specimen relative to the cutting blade 57 and makes a few trimming cuts. Afterwards, using the keyboard 73, he sets the thickness of the sections to be cut. Whatever thickness is selected is indicated on a digital screen 74. Finally, when he is ready to start cutting the specimen, the operator turns the handle 62. After each section has been cut, the specimen holder 20 is automatically raised by an increment of height which corresponds to the desired section thickness.

It is understood that those skilled in the art may conceive other applications, modifications and/or changes in the invention described above. Any such applications, modifications or changes which fall within the purview of the description are intended to be illustrative and not intended to be limitative. The scope of the invention is limited only by the scope of the claims appended hereto.

It is claimed:

1. A rotary microtome comprising:
   (a) a base;
   (b) a stationary shaft attached to the base;
   (c) a platform;
   (d) means including a cylindrical housing for rotatably supporting the platform, the cylindrical housing being rotatable about the shaft;
   (e) a specimen holder mounted on the platform;
   (f) an elongated knife holder;
   (g) means rigidly attached to the shaft for supporting a first end of the knife holder;
   (h) means rigidly attached to the base and disposed radially outside of the platform with respect to its path of rotation for supporting a second end of the knife holder;
   (i) a blade removably fitted into the knife holder;
   (j) means for rotating the platform through a revolution of 360 degrees so that the specimen holder passes under the blade; and
   (k) means for raising the specimen holder a predetermined distance above the platform, the holder raising means being used for positioning the specimen with respect to the blade.

2. The microtome according to claim 1 wherein the platform supporting means further comprises:
   (a) a bearing having an inner race, the bearing being press-fitted into the cylindrical housing and mounted on the stationary shaft so as to be juxtaposed between the housing and the shaft; and
   (b) means for reducing play in a radial direction between the housing and the shaft, the play reducing means including the shaft having a short tapered section and means for pressing the inner race of the bearing against the tapered section.

3. A rotary microtome for sectioning a specimen, comprising:
   (a) a specimen holder;
   (b) a platform;
   (c) means for mounting the specimen holder on the platform;
   (d) means for rotating the platform about a generally vertical axis;
   (e) a blade with a cutting edge;
   (f) means for mounting the blade so that its cutting edge is disposed generally perpendicularly to the axis of rotation of the platform, the platform traversing a circular path which is generally fixed in position with respect to the blade; and (g) mechanical means for raising the specimen holder relative to the platform in a predetermined increment of length, so that when the specimen comes into contact with the blade, a section of the specimen is cut to a uniform thickness.

4. A rotary microtome for sectioning a specimen, comprising:

(a) a specimen holder;

(b) a platform;

(c) means for mounting the specimen holder on the platform;

(d) means for rotating the platform about a generally vertical axis;

(e) a blade with a cutting edge;

(f) means for mounting the blade so that its cutting edge is disposed generally perpendicularly to the axis of rotation of the platform, the platform traversing a circular path which is generally fixed in position with respect to the blade; and (g) means for raising the specimen holder relative to the platform in a predetermined increment of length, so that when the specimen comes into contact with the blade, a section of the specimen is cut to a uniform thickness; the means for raising the specimen holder comprising a stepper motor mounted underneath the platform and connected thereto.

5. A rotary microtome comprising a base, a shaft connected to the base, a platform rotatable about the shaft, a knife holder, means rigidly attached to both the shaft and the base for supporting the knife holder, a blade removably fitted into the knife holder, a specimen holder, and means for slideably mounting the specimen holder on the platform so that the specimen holder is slideable in a direction generally parallel to the shaft.

* * * * *